(12) United States Patent
Nicholls

(10) Patent No.: US 8,603,126 B2
(45) Date of Patent: Dec. 10, 2013

(54) LANCET

(75) Inventor: Clive Nicholls, Buckinghamshire (GB)

(73) Assignee: Owen Mumford Limited, Woodstock, Oxfordshire (GB)

(*) Notice: Subject to any disclaimer, the term of this patent is extended or adjusted under 35 U.S.C. 154(b) by 223 days.

(21) Appl. No.: 12/161,985

(22) PCT Filed: Jan. 11, 2007

(86) PCT No.: PCT/GB2007/050011
§ 371 (c)(1),
(2), (4) Date: Jul. 24, 2008

(87) PCT Pub. No.: WO2007/085865
PCT Pub. Date: Aug. 2, 2007

(65) Prior Publication Data
US 2009/0012551 A1    Jan. 8, 2009

(30) Foreign Application Priority Data
Jan. 27, 2006    (GB) .................................. 0601695.0

(51) Int. Cl.
A61B 17/14    (2006.01)
(52) U.S. Cl.
USPC ......................................................... 606/181
(58) Field of Classification Search
USPC .......... 606/181, 185, 223, 182, 167; 600/583, 600/564, 566, 567; 604/192, 263; 30/340, 30/342
See application file for complete search history.

(56) References Cited

U.S. PATENT DOCUMENTS

| | | | |
|---|---|---|---|
| 5,207,699 A | 5/1993 | Coe | |
| 5,385,571 A * | 1/1995 | Morita | 606/181 |
| 5,730,753 A | 3/1998 | Morita | |
| 5,755,733 A * | 5/1998 | Morita | 606/182 |
| 6,053,930 A * | 4/2000 | Ruppert | 606/181 |
| 6,206,858 B1 * | 3/2001 | Kempen et al. | 604/218 |
| 6,358,265 B1 * | 3/2002 | Thorne et al. | 606/181 |
| 2004/0236251 A1 * | 11/2004 | Roe et al. | 600/583 |
| 2005/0131440 A1 | 6/2005 | Starnes | |
| 2005/0131441 A1 * | 6/2005 | Iio et al. | 606/182 |
| 2005/0283094 A1 | 12/2005 | Thym et al. | |

FOREIGN PATENT DOCUMENTS

| | | |
|---|---|---|
| EP | 0 137 975 | 4/1985 |
| EP | 0 589 186 | 3/1994 |

(Continued)

OTHER PUBLICATIONS

International Search Report for corresponding Application No. PCT/GB2007/050011 mailed Jun. 13, 2007.
British Search Report for corresponding Application No. GB0601695.0 dated Apr. 12, 2007.

(Continued)

*Primary Examiner* — Tuan V Nguyen
*Assistant Examiner* — Tin Nguyen
(74) *Attorney, Agent, or Firm* — Young & Thompson

(57) ABSTRACT

A skin pricking lancet (101) comprising a needle (104), a body (102) for holding the needle (104) and a cap (103) for shielding at least the tip of the needle (104). At least one cap engagement formation (106) is formed on the body (102), and at least one body engagement formation (108) is formed on the cap (103). The body engagement formation (106) is configured to form a releasable mechanical interlock with the cap engagement formation (108), thereby securing the cap (103) to the body (102) in the shielded position.

17 Claims, 2 Drawing Sheets

(56) References Cited

FOREIGN PATENT DOCUMENTS

Figure 1:
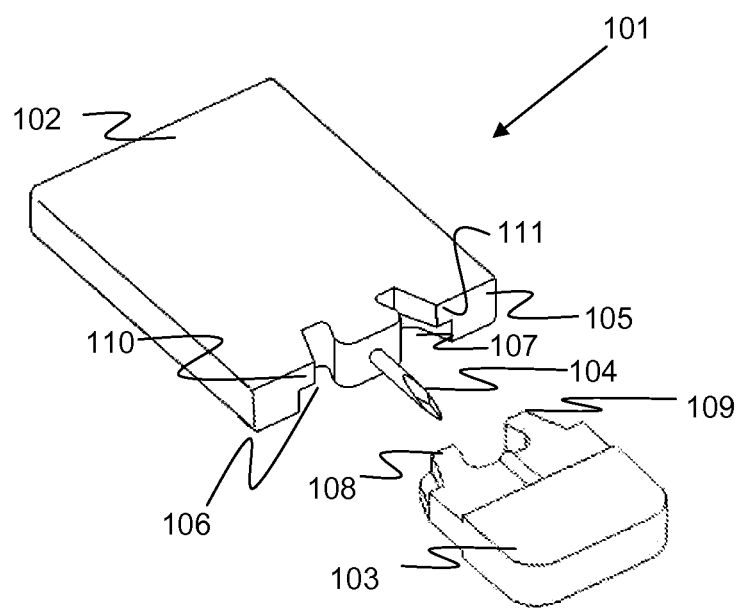

| | | |
|---|---|---|
| JP | 60063040 A | 4/1985 |
| JP | 0623505 U | 3/1994 |
| JP | 3638958 B2 | 1/2005 |
| WO | 96/16599 A1 | 6/1996 |
| WO | 9927855 A1 | 6/1999 |
| WO | 2006/096537 | 9/2006 |

OTHER PUBLICATIONS

Translation of Japanese Office Action, dated Mar. 27, 2012, from corresponding JP application No. 2008-551885.

Japanese Office Action, dated Feb. 26, 2013, from corresponding Japanese application.

* cited by examiner

LANCET

The present invention relates to skin pricking lancets, for example lancets for pricking skin to draw a droplet of blood.

Skin pricking lancets are well known in the art. Many such lancets comprise a needle having a sharp tip at one end and being embedded in a body at the opposite end, with the tip of the needle protruding from the body. The needle is usually made of metal. For the purpose of this specification, the end of the needle at which the tip is positioned will be referred to as the "distal" end, and the opposite end as the "proximal" end. The same terms will be used to designate the orientation or direction of other parts or movements described herein.

Skin pricking lancets are typically loaded into a firing device to prick the skin. The firing device may be disposable or reusable. Some firing devices can receive a plurality of lancets in the form of a stack or magazine of lancets for repeated use of the device. A user exposes the needle of the lancet by pressing a trigger.

Known lancets typically comprise a removable cap disposed on the distal end of the needle so as to maintain the sterility of the tip, as well as to protect the tip and the user prior to use. Typically, the cap is integrally moulded with the body, and a weakened "neck" area is provided to form the interface between the cap and the body. The cap is removed by twisting the cap relative to the body to break the neck, and then pulling the cap to remove it from the needle. Once such a cap has been removed, it is difficult to secure the cap back on the body in a position to shield the needle. Even though the cap may be pushed back onto the needle, this is not a secure attachment and the cap can easily slide away from the needle.

The cap need not be integrally moulded with the body, but may be formed as a separate component. Some such caps are solid components made from a soft material that are over-moulded on the needle.

According to a first aspect of the present invention, there is provided a skin pricking lancet comprising:
 a needle;
 a body for holding the needle; and
 a cap for shielding at least the tip of the needle;
 at least one cap engagement formation formed on the body; and
 at least one body engagement formation formed on the cap, the body engagement formation configured to form a releasable mechanical interlock with the cap engagement formation, thereby securing the cap to the body in the shielded position.

It is preferred that the interlocking body engagement formation and the cap engagement formation comprise interlocking male and female components.

Preferably, the body engagement formation comprises a pair of protrusions extending from the cap; and the cap engagement formation comprises a corresponding pair of openings in the body.

According to a preferred embodiment, the cap engagement formation comprises a first pair of ribs, and the body engagement formation comprises a second pair of ribs, wherein the first and second pairs of ribs are in blocking engagement with one another when the cap is in place to substantially prevent rotation of the cap relative to the body about the axis of the needle.

Preferably, the cap is made from a material that allows the needle to penetrate the cap during re-capping.

It is preferred that the cap is formed from a material selected from a thermoplastic elastomer, ethylene vinyl acetate, silicon rubber and low density polyethylene.

In a preferred embodiment, the body comprises low density polyethylene, high density polyethylene, polypropylene or polystyrene.

Preferably, the needle is embedded in both the body and the cap when the cap is secured to the body.

It is preferred that the body is moulded separately from the cap.

The body and the cap may be bonded together during moulding of the body or the cap. This provides a chemical bond between the body and the cap, in addition to the releasable mechanical interlock provided by the engagement of the body engagement formation with the cap engagement formation.

According to a second aspect of the present invention, there is provided a method of manufacturing a skin pricking lancet as described above, the method comprising the steps of:
 locating a portion of the needle in a mould; and
 injection moulding the body around the portion of the needle such that the tip of the needle protrudes from the body; and
 injection moulding the cap around at least the tip of the needle.

Figure 2:
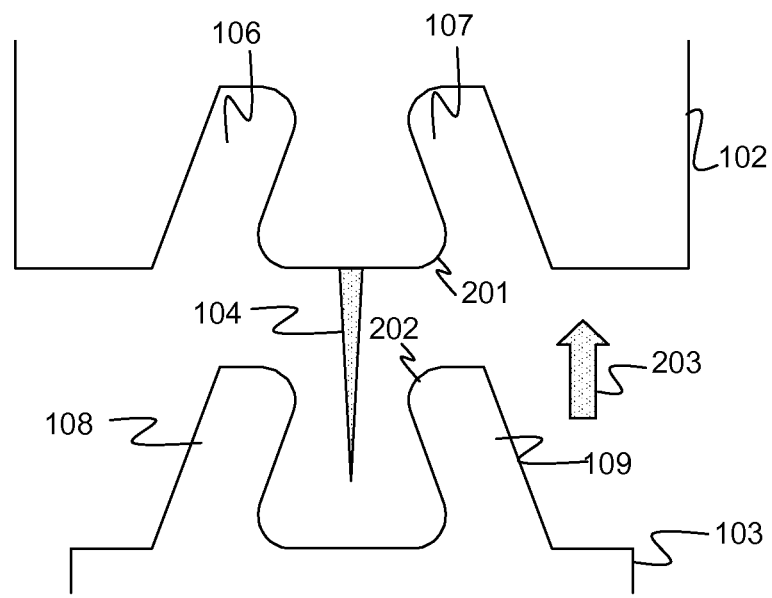
Figure 3:
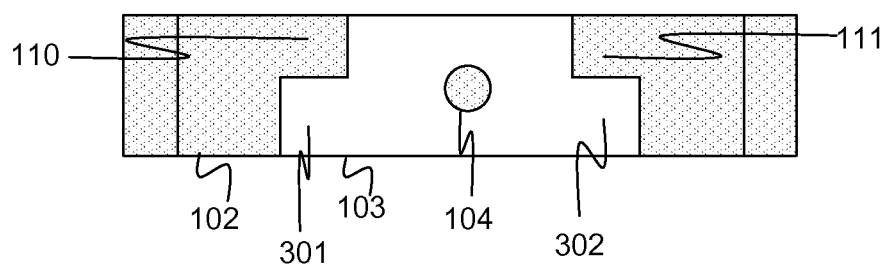

For a better understanding of the present invention and in order to show how the same may be carried into effect reference will now be made by way of example to the accompanying drawings in which:

FIG. 1 shows a perspective view of a lancet according to a first embodiment of the invention; and FIG. 2 shows schematically a plan view of the lancet of the first embodiment; and FIG. 3 shows a front elevation cross-section view of the lancet with the cap in place over the needle.

A lancet 101 according to a first embodiment of the invention as shown in FIG. 1 comprises a body 102, a cap 103 and a needle 104. The body 102 is injection moulded about the needle 104 such that the tip of the needle 104 projects from a distal end 105 of the body 102.

The body 101 is formed from a rigid plastics material, although any suitable material may be used. The materials that can be used for the body 102 include low density polyethylene, high density polyethylene, polypropylene and polystyrene. In this embodiment, a rigid plastics material is used as it can be easily injection moulded about the needle 104. The needle 104 is formed from a metal, although other materials such as plastics or ceramics may be used.

The cap 103 is formed from a soft, rubber-like material such as a thermoplastic elastomer, or ethylene vinyl acetate (EVA) or silicon rubber. The cap 103 comprises a body with a hole in which the needle 104 is disposed when the cap 103 is located on the needle 104. The hole may be preformed or may be made when the needle is pushed into the soft, rubber-like cap. Alternatively, the cap may be formed from a rigid plastics material such as low density polyethylene, although this would make recapping more difficult as the cap would need to be located accurately back in the hole.

The body 102 comprises two cap engagement formations 106, 107. The cap engagement formations 106, 107 comprise moulded openings in the distal end 105 of the body 102. The openings 106, 107 are "cut out" slots from the distal end 105 of the body that have a longitudinal axis that is at an angle to the main axis of the needle 104.

The cap 103 comprises two body engagement formations 108, 109 configured to interlock with the cap engagement formations 106, 107. The body engagement formations 108, 109 each comprise a projection from the cap 103, which has a longitudinal axis that is at an angle to the main axis of the needle 104 when the cap 103 is in place on the body 102.

The body engagement formations 108, 109 are formed to match the shape of the openings 106, 107 in the body 102, as shown in FIG. 2. Each opening 106, 107 has a curved portion 201, and each body engagement formation 108, 109 also has a curved portion 202.

Each engagement formation 106, 107, 108, 109 comprises a further cut-away section to provide anti-rotation ribs, as shown in FIG. 1 and more clearly in FIG. 3. Anti-rotation ribs 110, 111 are provided on each cap engagement formation 106, 107, and corresponding anti-rotation ribs 301, 302 are provided on each body engagement formation 108, 109.

The lancet 101 is manufactured by first disposing a portion of the needle 104 in a mould. The body 102 is then injection moulded about the needle 104 such that the tip of the needle 104 protrudes from the body 104. The cap 103 is subsequently overmoulded about the tip of the needle 104 to shield the needle 104 and maintain its sterility.

There is sufficient strength of bond between the body 102 and the needle 104 to hold the needle 104 in the body 102 during normal use of the lancet 101 or uncapping of the lancet 101. The strength of the bond between the needle 104 and the body 102 may be increased by roughening the surface of the needle 104 before moulding the body 102 around the needle 104.

When a user first obtains the lancet 101, the cap 103 is in place shielding the needle 104. In order to use the lancet, the cap 103 must be removed from the needle 104. This is achieved by pulling the cap 103 away from the body 102. As the cap 103 is pulled away from the body 102 the body engagement formations 108, 109 flex outwards with respect to the main axis of needle 104 owing to their elastic properties until they become disengaged from the cap engagement formations 106, 107, and the cap 103 can be removed from the needle 104. The lancet 101 is then ready to be used.

After use, it is desirable to replace the cap to reduce the risk of the needle 104 accidentally pricking the user or another person. To recap the needle 104, the cap 103 is slid towards the body 104 in the direction shown by arrow 203. The curved portions 201, 202 come into contact with each other and the direction of curvature deflects the body engagement formations 108, 109 outwards with respect to the needle 104. This deflection is possible owing to forming the cap from a rubber-like flexible material. As the cap 103 slides further towards the body, the body engagement formations 108, 109 slide into the corresponding cap engagement formations 106, 107. Once the body engagement formations 108, 109 are fully interlocked with the cap engagement formations 106, 107, the cap 103 is secured onto the body 102.

During recapping, the needle 104 either locates in a corresponding hole (not shown) in the cap 103, or penetrates the cap 103 to form a new hole.

When capping or uncapping the needle 104, the ribs 110, 111, 301, 302 cooperate to restrict rotational movement about the needle axis of the cap 103 relative to the body 104. It is desirable to restrict rotation of the cap during operation in an automatic device. Restricting rotation also allows a stack of lancets to stack more neatly because the cap is kept flat relative to the body.

Lancets of the type described herein may be used in firing devices including:
- a reusable firing device which can hold one lancet at a time; or
- a disposable firing device; or
- a firing device that accepts multiple lancets, for example in a magazine.

In the above description, reference is made to a user uncapping and recapping the lancet, but the uncapping and recapping operations can also be performed by a firing device that includes a mechanism to remove the cap from the needle and body, and/or a mechanism to replace the cap over the needle.

During manufacture, when the cap 103 is subsequently overmoulded about the tip of the needle, the cap 103 may from a bond with the body 104 at the interface between the cap 103 and the body 104. This reduces the risk of losing the sterility of the needle and provides a weak bond between the cap 103 and the body 104 in addition to the mechanical interlock provided. This eliminates the need for the use of adhesives to form a bond between the cap 103 and the body 104, although it is envisaged that adhesives could be additionally used if necessary.

It will be appreciated by those of skill in the art that various modifications may be made to the above described embodiments without departing from the scope of the present invention.

The invention claimed is:

1. A skin pricking lancet comprising:
   a needle;
   a body comprising a distal end for holding the needle;
   a removable cap shielding a tip of the needle and maintaining sterility of the tip of the needle;
   a cap engagement formation formed on the distal end of the body comprising a first plurality of ribs, and a plurality of openings defined in the distal end of the body and disposed adjacent the first plurality of ribs; and
   a body engagement formation formed on the removable cap comprising a second plurality of ribs and a plurality of protrusions disposed adjacent to the second plurality of ribs, the body engagement formation configured to form a releasable mechanical interlock with the cap engagement formation, thereby securing the removable cap to the body in the shielded position, and configured to allow the removable cap to be removed from the body prior to use of the lancet,
   wherein the body engagement formation and the cap engagement formation are arranged to restrict rotation of the removable cap relative to the body about a main axis of the needle, the first and second plurality of ribs being in blocking engagement with one another when the removable cap is in place to substantially prevent the rotation of the cap relative to the body about the axis of the needle, the cap being united with the body by slidingly engaging the plurality of protrusions within the plurality of openings, the first plurality of ribs at least partially covering the second plurality of ribs in an engaged state of the cap and the body, a portion of each of the first and second plurality of ribs being exposed to an outside environment of the lancet.

2. The lancet as claimed in claim 1, wherein the interlocking body engagement formation and the cap engagement formation comprise interlocking male and female components.

3. The lancet according to claim 1, wherein the removable cap is made from a material that allows the needle to penetrate the cap during re-capping.

4. The lancet according to claim 1, wherein the removable cap is formed from a material selected from a thermoplastic elastomer, ethylene vinyl acetate, silicon rubber and low density polyethylene.

5. The lancet according to claim 1, wherein the body comprises low density polyethylene, high density polyethylene, polypropylene or polystyrene.

6. The lancet according to claim 1, wherein the needle is embedded in both the body and the removable cap when the removable cap is secured to the body.

7. The lancet according to claim 1, wherein the body is molded separately from the removable cap.

8. The lancet according to claim 1, wherein the body and the removable cap are bonded together during molding of the body or the removable cap.

9. A skin pricking lancet comprising:
  a needle;
  a body comprising a distal end for holding the needle;
  a removable cap shielding a tip of the needle and maintaining sterility of the tip of the needle;
  a cap engagement formation formed on the distal end of the body, the cap engagement formation having a first anti-rotation rib, and at least one opening defined in the distal end of the body and disposed adjacent the first anti-rotation rib; and
  a body engagement formation formed on the removable cap, the body engagement formation having a second anti-rotation rib and at least one protrusion disposed adjacent the second anti-rotation rib, the body engagement formation configured to form a releasable mechanical interlock with the cap engagement formation, thereby securing the removable cap to the body in the shielded position, and configured to allow the removable cap to be removed from the body prior to use of the lancet,
  wherein the body engagement formation and the cap engagement formation are arranged to restrict rotation of the removable cap relative to the body about a main axis of the needle, the first and second anti-rotation ribs being in blocking engagement with one another when the removable cap is in place to substantially prevent the rotation of the cap relative to the body about the axis of the needle, the cap being united with the body by slidingly engaging the at least one protrusion within the at least one opening, the first anti-rotation rib at least partially covering the second anti rotation rib in an engaged state of the cap and the body, a portion of each of the first and second anti-rotation ribs being exposed to an outside environment of the lancet.

10. The lancet as claimed in claim 9, wherein the interlocking body engagement formation and the cap engagement formation comprise interlocking male and female components.

11. The lancet as claimed in claim 9, wherein the body engagement formation comprises a pair of the at least one protrusion extending from the removable cap, and the cap engagement formation comprises a corresponding pair of the at least one opening in the body.

12. The lancet according to claim 9, wherein the removable cap is made from a material that allows the needle to penetrate the cap during re-capping.

13. The lancet according to claim 9, wherein the removable cap is formed from a material selected from a thermoplastic elastomer, ethylene vinyl acetate, silicon rubber and low density polyethylene.

14. The lancet according to claim 9, wherein the body comprises low density polyethylene, high density polyethylene, polypropylene or polystyrene.

15. The lancet according to claim 9, wherein the needle is embedded in both the body and the removable cap when the removable cap is secured to the body.

16. The lancet according to claim 9, wherein the body is molded separately from the removable cap.

17. The lancet according to claim 9, wherein the body and the removable cap are bonded together during molding of the body or the removable cap.

\* \* \* \* \*